(12) United States Patent
Jean et al.

(10) Patent No.: US 10,330,664 B2
(45) Date of Patent: Jun. 25, 2019

(54) EVALUATION OF COMPONENT CONDITION THROUGH ANALYSIS OF MATERIAL INTERACTION

(71) Applicant: PRATT & WHITNEY CANADA CORP., Longueuil (CA)

(72) Inventors: Maurice Jean, Boucherville (CA); Daniel Meilleur, Boucherville (CA)

(73) Assignee: PRATT & WHITNEY CANADA CORP., Longueuil (CA)

( * ) Notice: Subject to any disclaimer, the term of this patent is extended or adjusted under 35 U.S.C. 154(b) by 592 days.

(21) Appl. No.: 14/743,015

(22) Filed: Jun. 18, 2015

(65) Prior Publication Data

US 2016/0370341 A1    Dec. 22, 2016

(51) Int. Cl.
    *G01N 33/28*    (2006.01)
    *H01J 37/28*    (2006.01)

(52) U.S. Cl.
    CPC .......... *G01N 33/2888* (2013.01); *H01J 37/28* (2013.01)

(58) Field of Classification Search
    CPC ................................................. G01N 33/2888
    USPC ....................................................... 73/114.55
    See application file for complete search history.

(56) References Cited

U.S. PATENT DOCUMENTS

| 3,751,661 | A | 8/1973 | Packer et al. |
| 3,981,584 | A | 9/1976 | Guymer |
| 5,517,427 | A | 5/1996 | Joyce |
| 5,537,336 | A | 7/1996 | Joyce |
| 5,586,161 | A | 12/1996 | Russell et al. |
| 5,817,928 | A | 10/1998 | Garvey, III et al. |
| 5,982,847 | A | 11/1999 | Nelson |
| 6,473,677 | B1 | 10/2002 | Hershey et al. |
| 6,598,464 | B1 | 7/2003 | Rossi |
| 6,643,570 | B2 | 11/2003 | Bangert et al. |
| 6,859,517 | B2 | 2/2005 | Wilson et al. |
| 7,184,515 | B2 | 2/2007 | Wilson |
| 7,523,615 | B2 | 4/2009 | Singh et al. |
| 7,634,913 | B2 | 12/2009 | Singh et al. |
| 7,689,368 | B2 | 3/2010 | Douglas |
| 7,745,382 | B2 | 6/2010 | Sloan |
| 8,522,604 | B2 | 9/2013 | Zhe et al. |
| 8,607,621 | B2 | 12/2013 | verdegan |

(Continued)

FOREIGN PATENT DOCUMENTS

| EP | 0672243 B1 | 3/2000 |
| EP | 2485037 B1 | 5/2015 |

(Continued)

OTHER PUBLICATIONS

US 6,435,103 B1, 08/2002, Rodriguez et al. (withdrawn)

(Continued)

*Primary Examiner* — Walter L Lindsay, Jr.
*Assistant Examiner* — Philipmarcus T Fadul
(74) *Attorney, Agent, or Firm* — Norton Rose Fulbright Canada LLP (57) ABSTRACT

There is described herein methods and systems relating to the use of the interaction of different materials to perform early detection of component failure. In particular, when the debris in a fluid sample comes from more than one source, a "level of interaction" is determined in order to monitor the degradation of the parts or components associated with the debris, as a function of the composition of the particles found in the fluid sample.

15 Claims, 7 Drawing Sheets

(56) References Cited

U.S. PATENT DOCUMENTS

| | | | |
|---|---|---|---|
| 8,676,436 | B2 | 3/2014 | Raimarckers et al. |
| 8,805,624 | B2 | 8/2014 | Uluyol |
| 8,862,433 | B2 | 10/2014 | Yerramalla et al. |
| 9,032,803 | B2 | 5/2015 | Griffaton |
| 9,244,042 | B2 | 1/2016 | Rank |
| 9,897,582 | B2 | 2/2018 | Jean et al. |
| 2008/0312384 | A1* | 12/2008 | Bruchmann ......... C08G 83/005 525/449 |
| 2010/0138132 | A1 | 6/2010 | Apps et al. |
| 2011/0095190 | A1* | 4/2011 | Kommareddy ...... G01N 23/207 250/364 |
| 2011/0125475 | A1 | 5/2011 | Lugt |
| 2012/0118051 | A1 | 5/2012 | Raadnui |
| 2012/0150491 | A1 | 6/2012 | Shi |
| 2012/0330499 | A1 | 12/2012 | Scheid et al. |
| 2013/0132034 | A1 | 5/2013 | Wilson |
| 2013/0197830 | A1 | 8/2013 | Dvorak |
| 2014/0121994 | A1* | 5/2014 | Jean ................... G01N 33/2858 702/27 |
| 2014/0324363 | A1 | 10/2014 | Reinman |
| 2015/0047419 | A1 | 2/2015 | Cao et al. |
| 2016/0093481 | A1 | 3/2016 | Bick et al. |
| 2016/0370341 | A1 | 12/2016 | Jean et al. |
| 2017/0159485 | A1 | 6/2017 | Jean et al. |

FOREIGN PATENT DOCUMENTS

| | | |
|---|---|---|
| JP | 10330779 | 12/1998 |
| WO | WO 2008013597 | 1/2008 |
| WO | 2015025160 A1 | 2/2015 |
| WO | WO 2015025160 A1 | 2/2015 |

OTHER PUBLICATIONS

Noria Corporation, "Using Electron Microscopy in Oil Analysis Applications—Comparing SEM to TEM", 6 pages. http://www.machinerylubrication.com/Read/698/electron-microscopy-sem-oil.

Golden, "The Determination of Iron in Used Lubricating Oil", Applied Spectroscopy, vol. 25, No. 6, Nov./Dec. 1971, pp. 668-671.

Herguth et al., "Applications of Scanning Electron. Microscopy and Energy Dispersive. Spectroscopy (SEM/EDS). To Practical Tribology Problems", Herguth Laboratories, 9 pages. http://www.herguth.com/technical/sem.pdf.

Vahaoja, "Oil Analysis in Machine Diagnostics", Acta Universitatis Ouluensis: A Scientiae Rerum Naturalium, vol. 458, University of Oulu, 2006, 80 pages.

Whitlock, "X-ray Methods for Monitoring Machinery Condition", Advances in X_ray Analysis, vol. 40, proceedings of the 45th Annual Denver X-ray Conferences, Aug. 1996, 12 pages.

Lukas et al., "Rotrode Filter Spectroscopy, Does It have a Place in Commercial or Military Oil Analysis Laboratory", Spectro Incorporated, Littleton, Massachusetts, 7 pages. http://protechanalytical.com/PDF%20files/RFS-4_98-1.pdf.

Eisentraut et al., "Spectrometrix Oil Analysis: Detecting Engine Failures Before They Occur", Analytical Chemistry, vol. 56, No. 9, Aug. 1984, pp. 1086A-1094A.

Farrant et al., "Effective Condition Monitoring of Aero-Engine Systems Using Automated SEM/EDX and New Diagnostic Routines", 1998, 14 pages.

Amsoil, "Correlation between particle size and engine wear", Technical service bulletin, A-F-2007-07-25, 3 pages. https://www.amsoil.com/techservicesbulletin/Aftermarket/TSB-AF-2007-07-25%20Oil%20filters%20Particle%20Size%20and%20Engine%20Wear.pdf.

Scientific and Techinal Information Center, "Search Report", STIC Database Tracking No. 487946, Jun. 19, 2014, 24 pages.

Levi O. et al. (2009) "Failure Analysis and Condition Monitoring of an Open-Loop Oil System Using Ferrography", Tribology Letters, vol. 36, No. 1. pages p. 17-29, (XP019734298).

European Search Report dated Jan. 3, 2017—European Patent Application No. 16191213.4.

Notice of Allowance dated Oct. 10, 2017, U.S. Appl. No. 13/661,181.

United States Patent and Trademark Office, Office Action, dated Apr. 4, 2018, 23 pages, U.S. Appl. No. 15/137,841.

* cited by examiner

EVALUATION OF COMPONENT CONDITION THROUGH ANALYSIS OF MATERIAL INTERACTION

TECHNICAL FIELD

The present invention relates generally to methods and systems for failure prediction using fluid analysis, and more particularly to methods and system for evaluating the condition of one or more components through the interaction of materials.

BACKGROUND OF THE ART

The analysis of engine oil or other lubricant for the purpose of identifying premature component wearing has been performed for several decades using optical atomic spectroscopy (e.g., atomic emission spectroscopy (AES), as well as atomic absorption spectroscopy (AAS)). This technology was the basis for the military aviation's Spectroscopic Oil Analysis Program (SOAP). However, it has certain disadvantages, such as a lack of repeatability among different equipment and an inability to analyze particles greater than 5 µm in diameter. Furthermore, optical atomic spectroscopy is an elemental analysis of the total oil sample and typically does not characterize individual particles in the sample.

Other approaches have since been proposed, whereby individual particles may be characterized and classified based on their chemical composition. However, these approaches are not sufficient to predict complex component failures.

SUMMARY

There is described herein methods and systems relating to the use of the interaction of different materials to perform early detection of component failure. In particular, when the debris in a fluid sample comes from more than one source, a "level of interaction" is determined in order to monitor the degradation of the parts or components associated with the debris, as a function of the composition of the particles found in the fluid sample.

In accordance with a first broad aspect, there is provided a method for evaluating a condition of at least one component from an environment having at least a first material and a second material different in chemical composition from the first material. The method comprises obtaining chemical composition data of a plurality of particles filtered from a fluid sample of the environment; identifying particles that fall within an interaction zone, the interaction zone corresponding to a concentration range for at least a first element found in the first material and at least a second element found in at least the second material, the concentration range defined by upper and lower limits that vary as a function of a given element, the upper limit corresponding to a minimum concentration for the given element in one of the first material and the second material, and the lower limit corresponding to a maximum concentration for the given element in the other of the first material and the second material; determining a level of interaction based on a quantity of particles within the interaction zone; and assigning a condition rating to the at least one component as a function of the level of interaction.

In accordance with another broad aspect, there is provided a system for evaluating a condition of at least one component from an environment having at least a first material and a second material different in chemical composition from the first material. The system comprises a memory; a processor coupled to the memory; and an application stored in the memory and executable by the processor. The application is executable for obtaining chemical composition data of a plurality of particles filtered from a fluid sample of the environment; identifying particles that fall within an interaction zone, the interaction zone corresponding to a concentration range for at least a first element found in the first material and at least a second element found in at least the second material, the concentration range defined by upper and lower limits that vary as a function of a given element, the upper limit corresponding to a minimum concentration for the given element in one of the first material and the second material, and the lower limit corresponding to a maximum concentration for the given element in the other of the first material and the second material; determining a level of interaction based on a quantity of particles within the interaction zone; and assigning a condition rating to the at least one component as a function of the level of interaction.

In accordance with yet another broad aspect, there is provided a non-transitory computer readable medium having stored thereon program code executable by a processor for carrying out the methods described herein.

BRIEF DESCRIPTION OF THE DRAWINGS

Further features and advantages of the present invention will become apparent from the following detailed description, taken in combination with the appended drawings, in which.

It will be noted that throughout the appended drawings, like features are identified by like reference numerals.

DETAILED DESCRIPTION

There is described herein methods and systems for evaluating the condition of at least one component based on materials interaction. The methods and systems are applicable to environments having two materials, or compositions, that are in contact with each other or that eventually come into contact with each other. The two materials may be found on two separate components or on a single component. The two components may be part of a mechanism whereby contact occurs through normal operation. The two components may also be part of a mechanism whereby contact occurs through abnormal operation, i.e. after some wear and tear to the mechanism. The two materials may be found on a single component, with the first material forming a first layer on the component and the second material forming a second layer on the component.

The one or more components may be any component that sheds particles upon contact, such as bearings, baffles, carbon seals, magnetic seals, and gears. The components may form part of a vehicle, such as an aircraft, a ship, a train, and an automobile, or be used for other applications, such as power plants, wind turbines, and damns. The environment may be an engine, such as a gas turbine engine, a turbojet engine, a turboprop engine, a turboshaft engine, or a turbofan engine, or any other environment whereby a fluid sample, such as a lubricant, may be obtained and filtered for particles.

The first material comprises at least a first element and the second material comprises at least a second element different from the first element. In some embodiments, each material is composed of only one element and the two elements differ, for example the first material is made of 100% copper and the second material is made of 100% iron. In some embodiments, both materials comprise the first element and the second element, but in different proportions. For example, the first material may comprise 70% of copper and 30% of zinc, and the second material may comprise 50% of copper and 50% of zinc. In some embodiments, the first material comprises more than one element and the second material comprises more than one element, and the first and second materials have no elements in common. In some embodiments, the first material comprises more than one element and the second material comprises more than one element, and the first and second materials have at least some elements in common. Other embodiments to which the methods and systems presented herein are applicable will be readily understood by the person skilled in the art.

Figure 1:
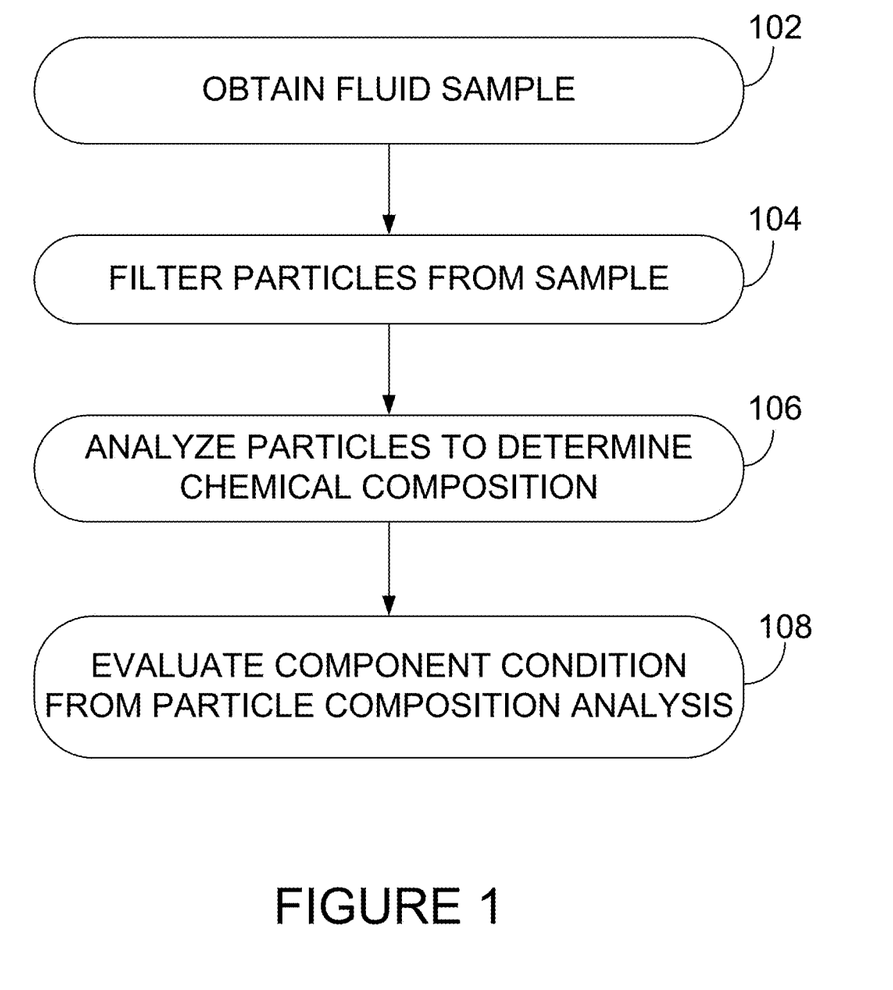
FIG. 1 is a flowchart of an exemplary method for failure prediction using fluid analysis.

FIG. 1 refers to a method for the analysis of fluid samples, such as engine oil (or other lubricant), in order to detect abnormal behavior, based on material wear, and predict potential failures. The method may, in some embodiments, be performed using the methods and system described by co-owned United States patent application bearing publication No. 2014/0121994, the contents of which are hereby incorporated by reference.

At 102, a fluid sample (e.g., an oil or other lubricant sample from an aircraft engine) is obtained. In the example of an oil sample from an aircraft engine, the oil sample may be collected by the aircraft operator. In some examples, more than one sample may be obtained from the engine. A relatively small amount of oil (e.g., 25 mL or less) may be sufficient. The amount of oil sample obtained may be selected in order to obtain a certain number of particles. For example, it may be known or expected that a given engine should have a certain density of particles in the oil after a certain number of operating hours. The volume of oil sample obtained may thus be determined in order to obtain a minimum quantity of particles. The frequency of sampling may be determined based on the flight hours per year, the maturity of the engine, the typical behavior of the engine type and/or the history of unscheduled engine removal for that engine type, for example. The sample may be obtained and prepared using any suitable method.

At 104, the sample is filtered using any suitable method to obtain particles from the sample. For example, a collected oil sample may be filtered using a very fine filter, such as a 0.22 μm filter, in order to filter out even very small particles (e.g., particles sized as small as 0.5 μm in diameter or smaller). Using such a filter, a sample of about 25 mL may produce a surface sample of about 16 mm in diameter. The particles obtained may range in size from about 0.5 μm to about 1600 μm, for example, although smaller or larger particles may also be obtained. The volume of oil sample filtrated and the size of the sample prepared may vary, such as according to the number of particles in the oil. The volume of oil sample that is filtered may be determined based on the type of engine and/or the expected normal levels of particles in the oil. In some examples, the obtained density of particles may be 500 particles per $mm^2$, which may be a density that can be used to reduce or avoid particles overlapping.

At 106, each particle is analyzed to determine a chemical composition. A scanning electron microscope (SEM) equipped to perform x-ray spectroscopy may be used for this analysis, although any other suitable methods may also be used. The SEM may be coupled to an X-Ray Fluorescence (XRF) detector for carrying out particle analysis. For example, an automated SEM, such as that from Aspex Corporation, may be used. The automated SEM may not require the presence of a human to select the particle that will be analyzed. Software and/or hardware in the system may automatically recognize the presence of a particle and may then automatically move the stage and the electron beam on the particle to perform the particle analysis. Any other suitable equipment may be used to perform this analysis.

A subset of the particles (e.g., 10% or less) may be analyzed while ensuring a good representation of the whole sample is captured. The analysis of the subset may be normalized to reflect the result for the full sample. For an average oil sample, about 1500 to 2000 particles may be analyzed. Suitable image analyzer software, such as those conventionally used with SEM, may be used to collect data about particle composition. Analysis of each particle may produce a respective set of data for that particle, for example there may be up to 70 data points for each particle, the data describing various features of the particle (e.g., size, shape and composition, among others).

At 108, the condition of one or more components from which the particles originate are evaluated as a function of the chemical composition of the particles in the sample. More specifically, the interaction of materials of different compositions are used to assess the condition of the one or more components.

Figure 2:
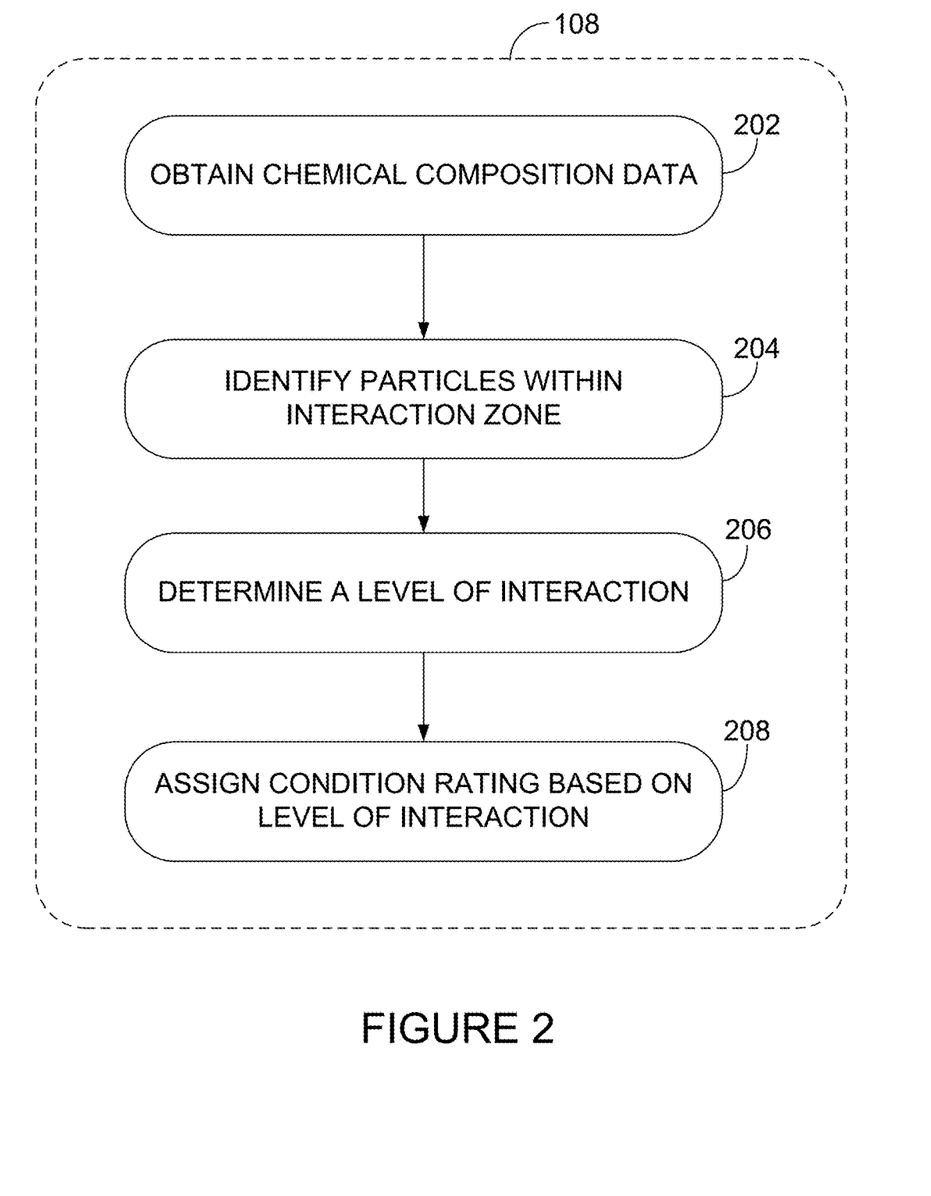
FIG. 2 is a flowchart of an exemplary method for evaluating component condition from a particle composition analysis.

FIG. 2 is an exemplary method for evaluating component condition based on materials interaction, as per 108. This method may be performed using any processor-based system, as will be explained in more detail below. Some particles found in the fluid sample cannot be classified as a specific material type because their composition is not within the defined concentration limits of the material. These particles may be the result of an interaction between two different materials, with a concentration for a given element higher than the maximum of one material and lower than the minimum of the other material. At 202, the chemical composition data previously determined at 106 is obtained. At 204, particles that fall within an interaction zone are identified. The interaction zone corresponds to a concentration range for the first element and the second element defined by upper and lower limits that vary as a function of a given element. The upper limit corresponds to a minimum concentration for the given element in the first material or the second material, and the lower limit corresponds to a maximum concentration for the given element in the other one of the first material or the second material. For example, if the Chromium concentration for a first material is from 4.0 to 7.0 and the Chromium concentration for a second material is from 10.0 to 13.0, the interaction zone will be from 7.0 to 10.0, with 7.0 being the maximum concentration for Chromium for the first material and 10.0 being the minimum concentration for Chromium for the second material. Thus a particle having a concentration for Chromium between 7.0 and 10.0 will be said to fall in the interaction zone and result from the interaction of the first material and the second material. If the concentration limits for a given element for the first material and the second material overlap, this element may be excluded from consideration. As such, particles are considered the result of an interaction between the first material and the second material if all of the concentrations of the main elements of the two materials are within an interaction zone.

In some embodiments, main elements are determined as follows: In materials comprising three or less elements, all elements may be considered main elements. In materials comprising four or five elements, elements having a concentration of about 2% or higher may be considered main elements. In materials having more than five elements, elements having a concentration of about 5% or higher may be considered main elements. Other embodiments for determining main elements may also be used.

Figure 3:
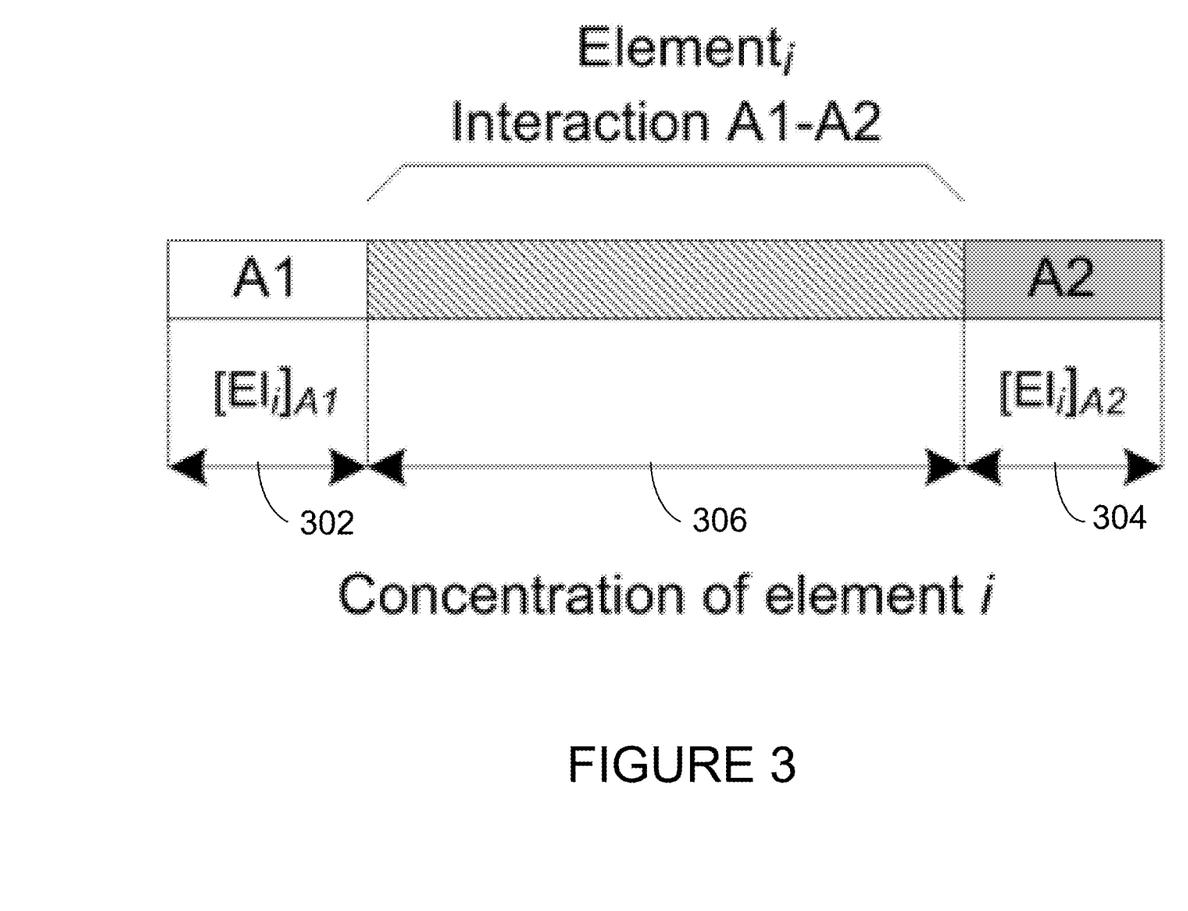
FIG. 3 is a schematic diagram illustrating an exemplary interaction zone between two materials.

FIG. 3 is provided to illustrate the principle of the interaction zone. $[El_i]_{A1}$ is the concentration range 302 for element i as part of the first material A1. $[El_i]_{A2}$ is the concentration range 304 for element i as part of the second material A2. For a given particle p, the concentration of a given element $[El_i]_p$ may be found to be within the limits of the concentration for this element in the first material A1 at 302, or within the limits of the concentration for this element in the second material A2 at 304. Otherwise, the concentration $[El_i]_p$ is said to be in the interaction zone 306 of the first material and the second material. Note that this exercise can be done for all elements that are found in A1 and A2.

In addition, an interaction zone may be formed from the interaction of more than two materials, such as three materials, four materials, or more. For example, assume that the first and second materials are composed as follows:

A1: Fe 70%; Ni 14%; Cr 10%
A2: Fe 50%; Ni 24%; Cr 20%

Also assume that the concentration limits for each element are ±2%, then any particles that are composed as follows will fall within the interaction zone:

P: Fe 53%-67%; Ni 17%-21%; Cr 13%-17%

Note that this example is provided with round numbers for simplicity. It may be that the boundaries of the interaction zone are set to several decimal points, such as 52.999%. It may also be that the boundaries of the interaction zone are set to be equal to the maximum and minimum concentration limits of the elements in the first and second material, such as 52% and 68% for Fe. The boundaries of the interaction zone may be set with greater or less precision, as desired. Other ways of setting the boundaries of the interaction zone may also be used.

Referring back to FIG. 2, at 206, a level of interaction of the two materials is determined based on a quantity of particles found within the interaction zone (IZ). The level of interaction is then associated with a given condition rating for the one or more components involved in the interaction of the first material and the second material, as per 208. For example, the level of interaction may be defined as follows:

TABLE 1

| # of Particles in IZ | Level of Interaction | Condition Rating |
|---|---|---|
| 0-50 | 1 | Normal |
| 51-150 | 2 | High |
| >150 | 3 | Critical |

The number of particles for each level of interaction may vary as a function of the volume of the fluid sample. They may also vary as a function of other factors, such as but not limited to the application, the materials, the compositions, and the mechanism involved in the contact between the materials. In addition, more or less levels and/or condition ratings may be used. For example, only two condition ratings defined as normal and abnormal may be used. In another example, four or more condition ratings may be used to provide a more granular evaluation of the interaction of the materials.

In some embodiments, determining a level of interaction may comprise determining a number of particles found in a subset of the interaction zone. The subset of the interaction zone may be a mix of the first and second materials according to a range of percentages from each material. For example, 30% of material 1+70% of material 2 to 40% of material 1+60% of material 2.

When considering just the elements themselves that are shared between the materials, the interaction zone may be defined as:

$IZ_{total}$: Fe 53%-67%; Ni 17%-21%; Cr 13%-17% and the subset of the interaction zone may be defined as:

$IZ_{subset}$: Fe 55%-60%; Ni 18%-20%; Cr 15%-16%

As such, only particles that have concentrations that fall within the subset of the interaction zone would be considered for determining a level of interaction. The subset may be determined using one or more factors, such as statistical analyses that establish what may be considered normal or abnormal in terms of the concentrations of particles found in the fluid sample, or based on historical observations. Other factors may also be used to determine the subset of the interaction zone.

In some embodiments, the subset of the interaction zone corresponds to a range of percentages of the first material and the second material that forms a given particle. In this case, determining the level of interaction comprises counting how many particles in the sample are composed of particles that fall within the predetermined range of percentages. For example, the subset of the interaction zone may comprise particles resulting from the contact of A1 and A2, containing between 20% and 80% of A1. Alternatively, the subset of the interaction zone may correspond to 5% to 15% of A1. The subset of the interaction zone, used to determine the level of interaction between A1 and A2, may be set as desired, using statistical analyses and/or historical observations. An example is illustrated in table 2.

TABLE 2

| # of Particles in $IZ_{subset}$ | Level of Interaction | Condition Rating |
|---|---|---|
| 0-50 | 5% | Normal |
| 51-150 | 15% | High |
| >150 | 25% | Critical |

In some embodiments, determining the percentage of the two or more materials that form a given particle may be performed mathematically, by minimizing the following equation:

$$\sum_{i=1}^{n} ([El_i]_p - (P_{A1}[El_i]_{A1} + P_{A2}[El_i]_{A2}))^2$$

while $P_{A1}$ $P_{A2}=1$, where $P_{A1}$ is a percentage of the first material in the given particle, $P_{A2}$ is a percentage of the second material in the given particle, n is a number of elements considered, $[El_i]$ is a concentration of element i, p is a particle, A1 is the first material, and A2 is the second material. The equation is minimized for every particle $P_{A1}$ varying from 0 to 1 (or from 0% to 100%).

Several methods may be used to minimize the equation. For example, a second degree equation in the form of $y=ax^2+bx+c$ may be calculated from specific data points. Using the example from above with a particle i having the following composition:

A1: Fe 70%; Ni 14%; Cr 10%
A2: Fe 50%; Ni 24%; Cr 20%
Particle i: Fe 62%; Ni 20%; Cr 17%

Figure 4:
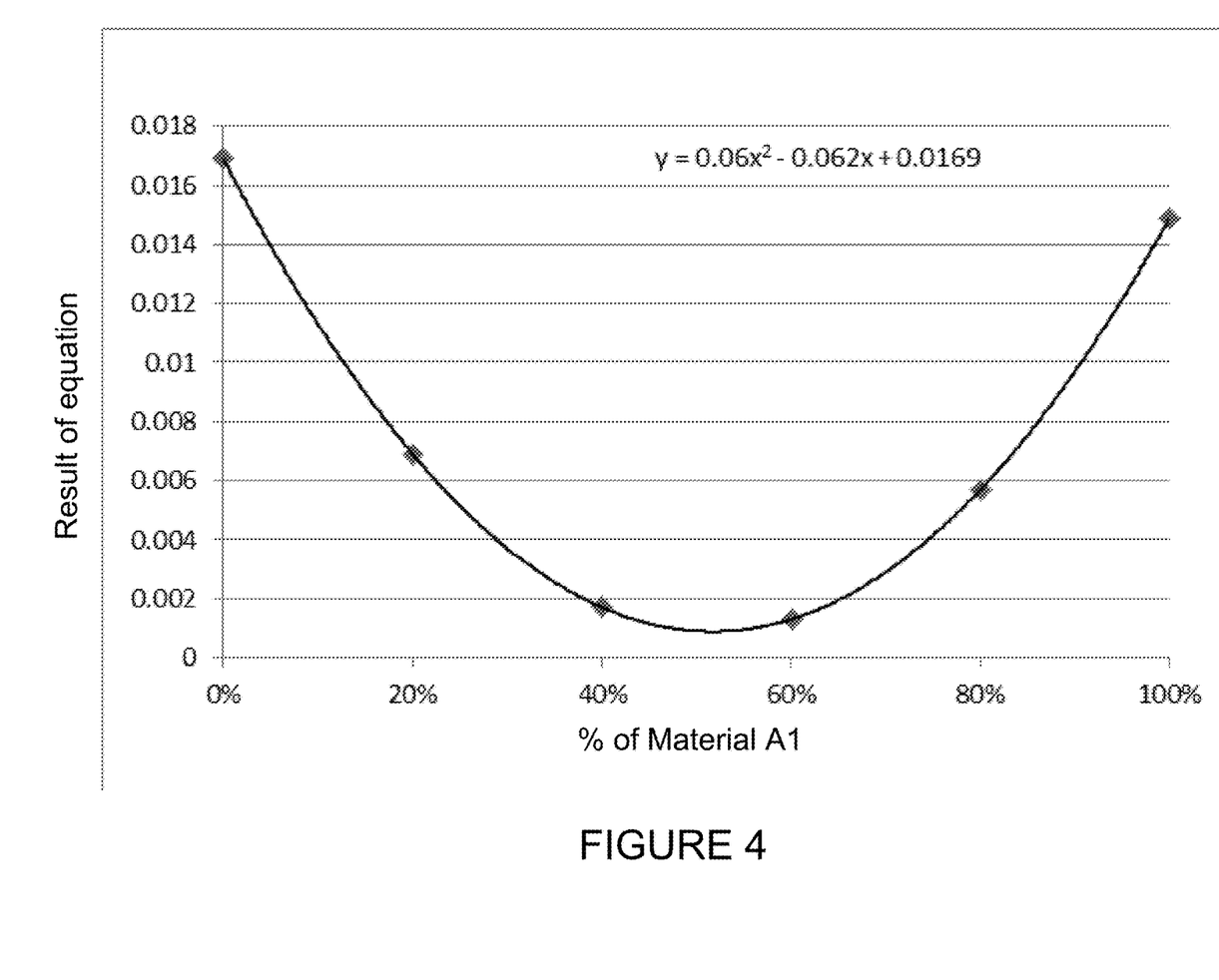
FIG. 4 is a graph of the percent of a material in a given particle versus a minimized function.

A data set comprising a given number of hypotheses may be used. More or less data points may be used to obtain a more or less precise result. An example where the function is determined using six hypothetical compositions is illustrated below:

$(P_{A1}, P_{A2})=(100\%, 0\%);\ \Sigma_{i=1}{}^n([El_i]_p-(P_{A1}[El_i]_{A1}+P_{A2}[El_i]_{A2}))^2=0.0149$ $(P_{A2}, P_{A2})=(80\%, 20\%);\ \Sigma_{i=1}{}^n([El_i]_p-(P_{A1}[El_i]_{A1}+P_{A2}[El_i]_{A2}))^2=0.0057$ $(P_{A2}, P_{A2})=(60\%, 40\%);\ \Sigma_{i=1}{}^n([El_i]_p-(P_{A1}[El_i]_{A1}+P_{A2}[El_i]_{A2}))^2=0.0013$ $(P_{A2}, P_{A2})=(40\%, 60\%);\ \Sigma_{i=1}{}^n([El_i]_p-(P_{A1}[El_i]_{A1}+P_{A2}[El_i]_{A2}))^2=0.0017$ $(P_{A2}, P_{A2})=(20\%, 80\%);\ \Sigma_{i=1}{}^n([El_i]_p-(P_{A1}[El_i]_{A1}+P_{A2}[El_i]_{A2}))^2=0.0069$ $(P_{A2}, P_{A2})=(0\%, 100\%);\ \Sigma_{i=1}{}^n([El_i]_p-(P_{A1}[El_i]_{A1}+P_{A2}[El_i]_{A2}))^2=0.0169$ FIG. 4 is a graph of the resulting function, which may be represented by the second degree equation $y=0.06x-0.062x+0.0169$, and its minimum $(-b/2a)$ is 0.517. The particle i is thus considered to be composed of 51.7% of material A1 and 48.3% of material A2. Depending on the predetermined range established as the subset of the interaction zone, particle i may be considered to fall within or outside of the subset of the interaction zone.

Material interaction may thus be quantified and characterized in order to monitor the degradation of components. The level of interaction is determined by the quantity of particles within the interaction zone or within a subset of the interaction zone. Depending on the application and the criticality of the interaction, different zones may be used. Once the level of interaction is quantified, knowledge of a failure mechanism may be used to observe various patterns. For example, consider the following pattern:

Step 1: Part A made of Series 300 stainless steel is moving slightly on Part B made of aluminum alloy.
Step 2: Part A moves more freely and touches Part C (a stud) made of High Nickel Stainless Steel.
Step 3: Part B start to move freely and rubs against Part C.
Step 4: Part B is fretting on Part D, made of low alloy.
Step 5: Part B is degrading.
Step 6: Failure of Part B.

Quantifying the interaction between the different materials involved in the pattern allows this pattern to be recognized early on in the process. In order to prevent failure of Part B during normal operation, detection of interaction of materials involved in steps 1, 2, or 3 may be used. Such detection may allow replacement of Part B before failure, thus leading to reduced damages and/or lower replacement costs. In addition, the interaction of Part A with Part B may be detected and lead to maintenance which may prevent the interaction between Part A and Part C, at step 2. Testing frequency may be increased to monitor various steps of a given pattern, such as steps 3, 4, and 5 in the above example. Recommendations for the replacement of defective or degrading parts may be made during the process, based on the estimated time of failure.

In some embodiments, the presence of some material, such as silver plating, may be considered critical due to the origin of the material, i.e. its use in bearing assembly. For example, if the silver plating is linked to a high nickel stainless steel, it may be related to lubricating plating on a bolt. If instead the silver plating is linked to a low alloy steel, it may come from a bearing cage. The ability to identify a source of the material provides added information useful to the prediction of failure of a given mechanism.

Figure 5:
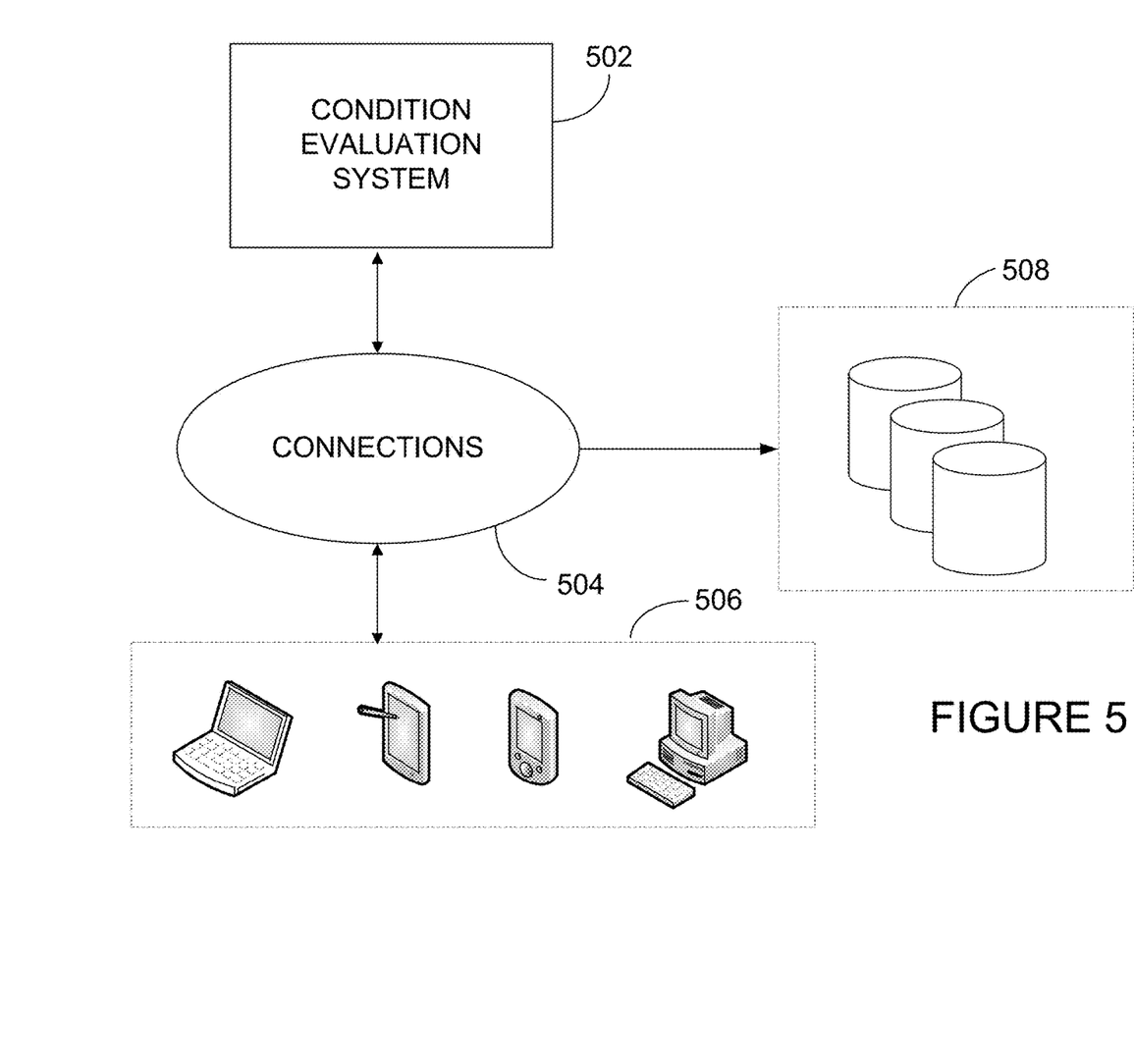
FIG. 5 is a diagram illustrating an exemplary system for evaluating the condition of a component.

Referring now to FIG. 5, a system for evaluating component condition will now be described. The system 502, may be accessible remotely from any one of a plurality of devices 506 over connections 504. The connections 504 may comprise wire-based technology, such as electrical wires or cables, and/or optical fibers. The connections 504 may also be wireless, such as RF, infrared, Wi-Fi, Bluetooth, and others. Connections 504 may therefore comprise a network, such as the Internet, the Public Switch Telephone Network (PSTN), a cellular network, or others known to those skilled in the art. Communication over the network may occur using any known communication protocols that enable devices within a computer network to exchange information. Examples of protocols are as follows: IP (Internet Protocol), UDP (User Datagram Protocol), TCP (Transmission Control Protocol), DHCP (Dynamic Host Configuration Protocol), HTTP (Hypertext Transfer Protocol), FTP (File Transfer Protocol), Telnet (Telnet Remote Protocol), SSH (Secure Shell Remote Protocol). The devices 506 may comprise any device, such as a personal computer, a tablet, a smart phone, or the like, which is configured to communicate over the connections 504. In some embodiments, the condition evaluation system 502 may itself be provided directly on one of the devices 506, either as a downloaded software application, a firmware application, or a combination thereof.

One or more databases 508 may be integrated directly into the system 502 or any one of the devices 508, or may be provided separately therefrom (as illustrated). In the case of a remote access to the databases 508, access may occur via connections 504 taking the form of any type of network, as indicated above. The various databases 508 described herein may be provided as collections of data or information organized for rapid search and retrieval by a computer. The databases 508 may be structured to facilitate storage, retrieval, modification, and deletion of data in conjunction with various data-processing operations. The databases 508 may be any organization of data on a data storage medium, such as one or more servers. The databases 508 illustratively have stored therein raw data representing a plurality of features of the particles filtered from the fluid sample obtained, the features being for example physical characteristics and chemical composition. The databases 508 may also have stored thereon specific chemical composition data from particle analysis, data defining an interaction zone and/or a subset of an interaction zone, levels of interaction, condition ratings, and the outcomes of the evaluation of the condition of components.

Figure 6:
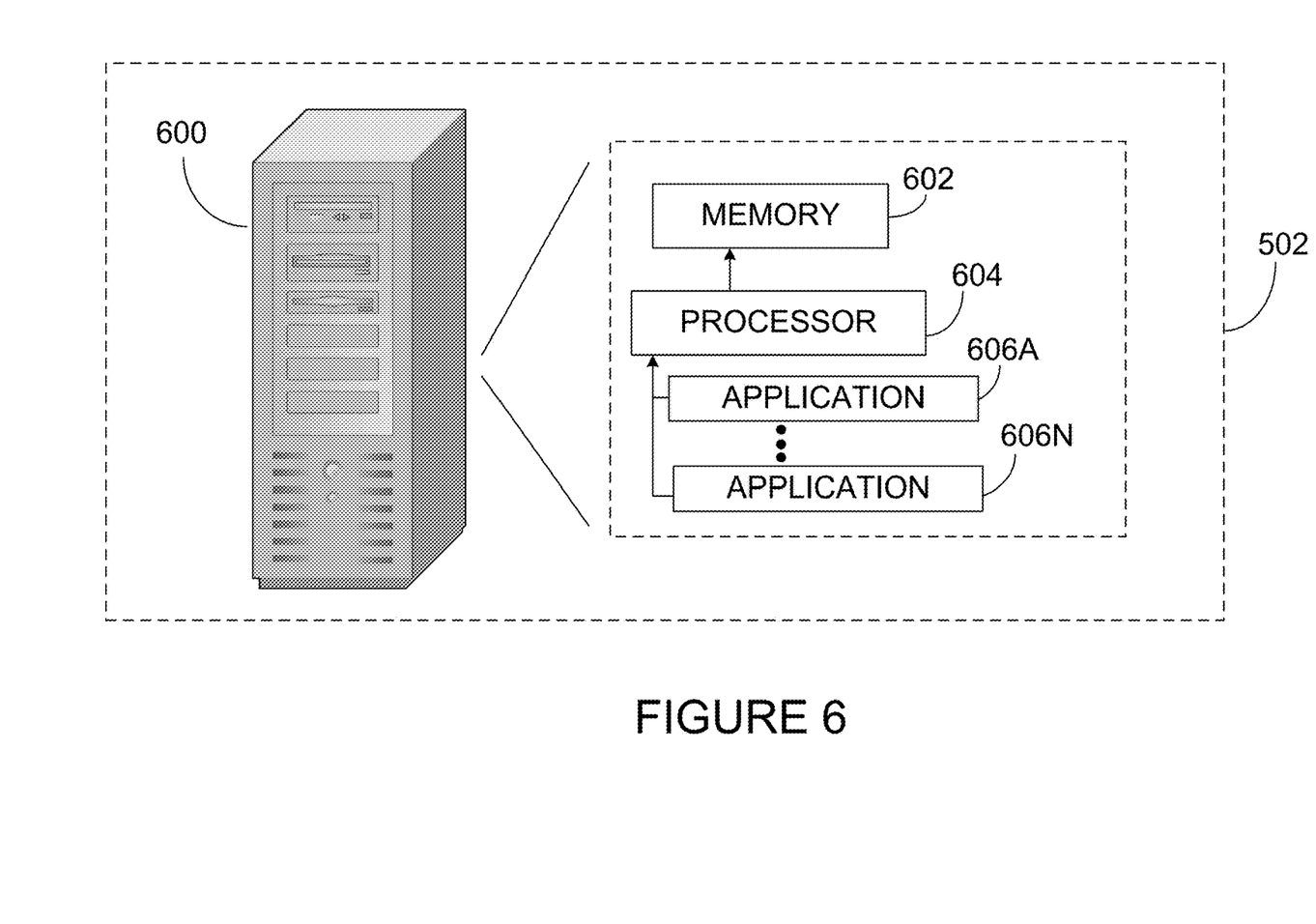
FIG. 6 is an exemplary embodiment of the condition evaluation system.

As shown in FIG. 6, the system 502 illustratively comprises one or more server(s) 600. The server 600 may be accessed by a user, such as a technician or an lab employee, using one of the devices 506, or directly on the system 502 via a graphical user interface. The server 600 may comprise, amongst other things, a plurality of applications 606a . . . 606n running on a processor 604 coupled to a memory 602. It should be understood that while the applications 606a . . . 606n presented herein are illustrated and described as separate entities, they may be combined or separated in a variety of ways.

The memory 602 accessible by the processor 604 may receive and store data. The memory 602 may be a main memory, such as a high speed Random Access Memory (RAM), or an auxiliary storage unit, such as a hard disk, a floppy disk, or a magnetic tape drive. The memory 602 may be any other type of memory, such as a Read-Only Memory (ROM), or optical storage media such as a videodisc and a compact disc. The processor 604 may access the memory 602 to retrieve data. The processor 604 may be any device that can perform operations on data. Examples are a central processing unit (CPU), a front-end processor, a microprocessor, and a network processor. The applications 606a . . . 606n are coupled to the processor 604 and configured to perform various tasks. An output may be transmitted to devices 506.

Figure 7:
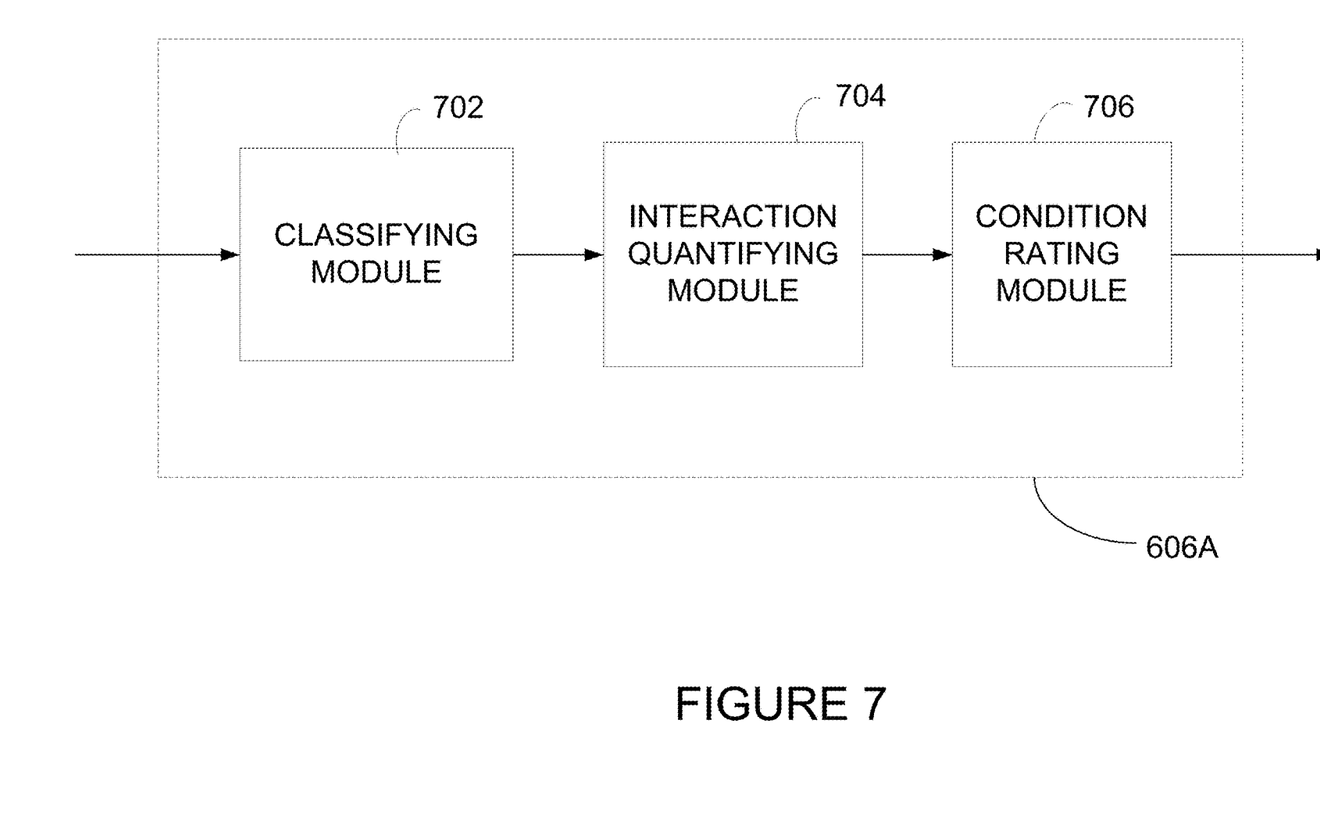
FIG. 7 is an exemplary embodiment of an application running on the system of FIG. 6.

FIG. 7 is an exemplary embodiment of an application 606a running on the processor 604. The application 606a illustratively comprises a classifying module 702, an interaction quantifying module 704, and a condition rating module 706. The classifying module 702 is configured to obtain the chemical composition data from the filtered particles. It may obtain them by requesting that they be provided from another source, or it may obtain them by receipt thereof without prompt. In some embodiments, the classifying module 702 may also be configured to analyze the particles from the filtered fluid sample in order to generate the chemical composition data. Once obtained, the chemical composition data is used by the classifying module to identify particles that fall within the interaction zone, as described above. This identification step may be considered as a classification of particles, wherein some particles are classified as resulting from an interaction between at least two materials when the composition thereof meets the criteria for the interaction zone or the subset of the interaction zone. The classifying module 702 may then transmit the classification data to the interaction quantifying module 704.

The interaction quantifying module 704 may be configured to determine the level of interaction based on the quantity of particles within the interaction zone, as described above. The level of interaction is provided to the condition rating module 706, which may be configured to assign a condition rating to the one or more components involved in the material interaction, as a function of the level of interaction.

In some embodiments, a non-transitory computer readable medium having stored thereon program code executable by a processor for carrying out the methods described herein and illustrated in application 606a may be provided.

The above description is meant to be exemplary only, and one skilled in the relevant arts will recognize that changes may be made to the embodiments described without departing from the scope of the invention disclosed. For example, the blocks and/or operations in the flowcharts and drawings described herein are for purposes of example only. There may be many variations to these blocks and/or operations without departing from the teachings of the present disclosure. For instance, the blocks may be performed in a differing order, or blocks may be added, deleted, or modified.

While illustrated in the block diagrams as groups of discrete components communicating with each other via distinct data signal connections, it will be understood by those skilled in the art that the present embodiments are provided by a combination of hardware and software components, with some components being implemented by a given function or operation of a hardware or software system, and many of the data paths illustrated being implemented by data communication within a computer application or operating system. The structure illustrated is thus provided for efficiency of teaching the present embodiment. The present disclosure may be embodied in other specific forms without departing from the subject matter of the claims. Also, one skilled in the relevant arts will appreciate that while the systems, methods and computer readable mediums disclosed and shown herein may comprise a specific number of elements/components, the systems, methods and computer readable mediums may be modified to include additional or fewer of such elements/components. The present disclosure is also intended to cover and embrace all suitable changes in technology. Modifications which fall within the scope of the present invention will be apparent to those skilled in the art, in light of a review of this disclosure, and such modifications are intended to fall within the appended claims.

The invention claimed is:

1. A method for evaluating a condition of at least one component from an environment having at least a first material and a second material different in chemical composition from the first material, the method comprising:
    obtaining chemical composition data of a plurality of particles filtered from a fluid sample of the environment;
    identifying particles that fall within an interaction zone, the interaction zone corresponding to a concentration range for at least a first element found in the first material and at least a second element found in at least the second material, the concentration range defined by upper and lower limits that vary as a function of a given element, the upper limit corresponding to a minimum concentration for the given element in the first material and the lower limit corresponding to a maximum concentration for the given element in the second material;
    determining a level of interaction based on a quantity of particles within the interaction zone, comprising:
        determining a percentage of the first material and a percentage of the second material that forms a given particle by minimizing an equation, for every particle, for a concentration of the first material from zero to 100%, the equation comprising:

$$\sum_{i=1}^{n} ([El_i]_p - (P_{A1}[El_i]_{A1} + P_{A2}[El_i]_{A2}))^2$$

while $P_{A1}+P_{A2}=1$, where $P_{A1}$ is a percentage of the first material in the given particle, $P_{A2}$ is a percentage of the second material in the given particle, n is a number of elements considered, [El$_i$] is a concentration of element i, p is a particle, A1 is the first material, and A2 is the second material; and counting how many particles in the sample are composed of a predetermined range of concentrations of the first material and the second material; and assigning a condition rating to the at least one component as a function of the level of interaction.

2. The method of claim 1, wherein the first element and the second element are found in the first material and the second material at different concentrations.

3. The method of claim 1, wherein determining a level of interaction comprises identifying a quantity of particles within a subset of the interaction zone.

4. The method of claim 3, wherein the subset of the interaction zone corresponds to a critical zone based on historical observations.

5. The method of claim 1, wherein the first material is a first alloy and the second material is a second alloy.

6. The method of claim 5, wherein the first alloy is on a first component and the second alloy is on a second component.

7. The method of claim 1, wherein the environment is an engine and the fluid sample is a lubricant of the engine.

8. A system for evaluating a condition of at least one component from an environment having at least a first material and a second material different in chemical composition from the first material, the system comprising:

a memory;

a processor coupled to the memory; and an application stored in the memory and executable by the processor for:

obtaining chemical composition data of a plurality of particles filtered from a fluid sample of the environment;

identifying particles that fall within an interaction zone, the interaction zone corresponding to a concentration range for at least a first element found in the first material and at least a second element found in at least the second material, the concentration range defined by upper and lower limits that vary as a function of a given element, the upper limit corresponding to a minimum concentration for the given element in the first material and the lower limit corresponding to a maximum concentration for the given element in the second material;

determining a level of interaction based on a quantity of particles within the interaction zone, comprising:

determining a percentage of the first material and a percentage of the second material that forms a given particle by minimizing an equation, for every particle, for a concentration of the first material from zero to 100%, the equation comprising:

$$\sum_{i=1}^{n}([El_i]_p - (P_{A1}[El_i]_{A1} + P_{A2}[El_i]_{A2}))^2$$

while $P_{A1}+P_{A2}=1$, where $P_{A1}$ is a percentage of the first material in the given particle, $P_{A2}$ is a percentage of the second material in the given particle, n is a number of elements considered, [El$_i$] is a concentration of element i, p is a particle, A1 is the first material, and A2 is the second material; and counting how many particles in the sample are composed of a predetermined range of concentrations of the first material and the second material; and assigning a condition rating to the at least one component as a function of the level of interaction.

9. The method of claim 8, wherein the first element and the second element are found in the first material and the second material at different concentrations.

10. The system of claim 9, wherein determining a level of interaction comprises identifying a quantity of particles within a subset of the interaction zone.

11. The system of claim 10, wherein the subset of the interaction zone corresponds to a critical zone based on historical observations.

12. The system of claim 8, wherein the first material is a first alloy and the second material is a second alloy.

13. The system of claim 12, wherein the first alloy is on a first component and the second alloy is on a second component.

14. The system of claim 8, wherein the environment is an engine and the fluid sample is a lubricant of the engine.

15. A non-transitory computer readable medium having stored thereon program code executable by a processor for carrying out a method for evaluating a condition of at least one component from an environment having at least a first material and a second material different in chemical composition from the first material, the program code comprising instructions for:

obtaining chemical composition data of a plurality of particles filtered from a fluid sample of the environment;

identifying particles that fall within an interaction zone, the interaction zone corresponding to a concentration range for at least a first element found in the first material and at least a second element found in at least the second material, the concentration range defined by upper and lower limits that vary as a function of a given element, the upper limit corresponding to a minimum concentration for the given element in the first material and the lower limit corresponding to a maximum concentration for the given element in the second material;

determining a level of interaction based on a quantity of particles within the interaction zone, comprising:

determining a percentage of the first material and a percentage of the second material that forms a given particle by minimizing an equation, for every particle, for a concentration of the first material from zero to 100%, the equation comprising:

$$\sum_{i=1}^{n}([El_i]_p - (P_{A1}[El_i]_{A1} + P_{A2}[El_i]_{A2}))^2$$

while $P_{A1}+P_{A2}=1$, where $P_{A1}$ is a percentage of the first material in the given particle, $P_{A2}$ is a percentage of the second material in the given particle, n is a number of elements considered, [El$_i$] is a concentration of element i, p is a particle, A1 is the first material, and A2 is the second material; and counting how many particles in the sample are composed of a predetermined range of concentrations of the first material and the second material; and assigning a condition rating to the at least one component as a function of the level of interaction.

* * * * *